United States Patent [19]

Benavides et al.

[11] Patent Number: 4,728,647
[45] Date of Patent: Mar. 1, 1988

[54] AMIDES DERIVED FROM QUINOLINE, AND ANXIOLYTIC COMPOSITIONS CONTAINING THEM

[75] Inventors: Jesus Benavides, Rueil-Malmaison; Marie-Christine Dubroeucq, Enghien-Les-Bains; Gérard Le Fur, Montmorency; Christian Renault, Taverny, all of France

[73] Assignee: Rhone-Poulenc Sante, Courbevoie, France

[21] Appl. No.: 867,474

[22] Filed: May 28, 1986

[30] Foreign Application Priority Data

May 30, 1985 [FR] France .................. 85 08111

[51] Int. Cl.$^4$ .................. A61K 31/47; C07D 215/22
[52] U.S. Cl. .................. 514/222; 514/227; 514/247; 514/312; 514/314; 544/62; 544/125; 544/164; 544/363; 546/153
[58] Field of Search .............. 546/153, 167, 173, 176, 546/180, 170, 175, 272; 514/312, 313, 314, 222, 227, 247; 562/471; 564/182; 544/358, 125, 59, 362, 121, 362, 106, 62; 549/59

[56] References Cited

U.S. PATENT DOCUMENTS

| | | | |
|---|---|---|---|
| 2,568,037 | 9/1951 | Surrey | 546/153 |
| 2,785,165 | 3/1957 | Schock | 546/153 |
| 4,252,804 | 2/1981 | Joullié | 514/311 |
| 4,402,961 | 9/1983 | Dubroeucq | 546/167 |
| 4,433,150 | 2/1984 | Champseix | 546/176 |

FOREIGN PATENT DOCUMENTS

| | | | |
|---|---|---|---|
| 2253743 | 7/1975 | France . | |
| 4115702 | 5/1966 | Japan | 546/153 |
| 1013224 | 12/1965 | United Kingdom | 546/153 |
| 1064252 | 4/1967 | United Kingdom . | |
| 1177548 | 1/1970 | United Kingdom . | |

OTHER PUBLICATIONS

Burger, A., *Medicinal Chemistry*, Interscience Publishers, Inc., New York, N.Y., (1960), pp. 42 and 44-45.
Irikura, T. et al., *Chemical Abstracts*, v.67, 1967, p. 3102, CA No. 67: 32700c.
FR-M-8411 (Anvar Resume, Point 1.

*Primary Examiner*—Donald G. Daus
*Assistant Examiner*—Mark W. Noel
*Attorney, Agent, or Firm*—Stevens, Davis, Miller & Mosher

[57] ABSTRACT

Compounds of formula:

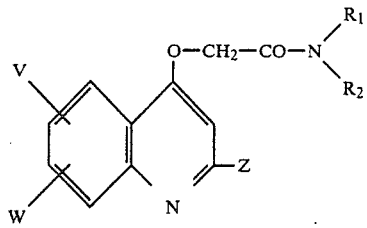

in which
V and W are H, halogen, alkyl (1–4C) or alkoxy (1–4C), amino, or acylamino,
Z is phenyl, optionally substituted, thienyl, or pyridyl,
$R_1$ is alkyl (1–6C), alkoxyalkyl, cycloalkyl (3–6C), phenyl, phenylalkyl, or cycloalkylalkyl,
$R_2$ is alkyl (1–6C), alkoxyalkyl, cycloalkyl (3–6C), phenyl, phenylalkyl, cycloalkylalkyl, or morpholino, and
$NR_1R_2$ can also be pyrrolidino, optionally substituted piperidino, optionally substituted morpholino, thiomorpholino, optionally substituted piperazino, or an optionally substituted piperazinone, are useful as anxiolytic agents.

9 Claims, No Drawings

AMIDES DERIVED FROM QUINOLINE, AND ANXIOLYTIC COMPOSITIONS CONTAINING THEM

The present invention relates to amides derived from quinoline, their preparation, and pharmaceutical compositions containing them.

The compounds of the invention are those of the formula:

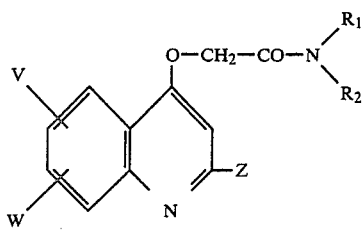

in which:
- V and W, which may be identical or different, denote hydrogen, halogen (fluorine, chlorine, bromine), alkyl of 1 to 4 carbon atoms, alkoxy of 1 to 4 carbon atoms, amino or acylamino of 1 to 4 carbon atoms,
- Z denotes phenyl, thienyl, pyridyl, or phenyl substituted by one or two substituents selected from halogen, alkyl of 1 to 4 carbon atoms, alkoxy of 1 to 4 carbon atoms, trifluoromethyl, nitro or amino,
- $R_1$ denotes a linear or branched alkyl of 1 to 6 carbon atoms, alkoxyalkyl in which the alkoxy and alkyl each contain 1 to 4 carbon atoms, cycloalkyl of 3 to 6 carbon atoms, phenyl, phenylalkyl in which the alkyl contains 1 to 4 carbon atoms, or cycloalkylalkyl in which the alkyl portion contains 1 to 3 carbon atoms and the cycloalkyl portion contains 3 to 6 carbon atoms,
- $R_2$ denotes a linear or branched alkyl of 1 to 6 carbon atoms, alkoxyalkyl in which the alkoxy and alkyl portions each contain 1 to 4 carbon atoms, cycloalkyl of 3 to 6 carbon atoms, phenyl, phenylalkyl in which the alkyl contains 1 to 4 carbon atoms, or cycloalkylalkyl in which the alkyl portion contains 1 to 3 carbon atoms and the cycloalkyl portion contains 3 to 6 carbon atoms, or a 4-morpholine ring, and
- $R_1$ and $R_2$ can also form, together with the nitrogen atom to which they are attached: pyrrolidino; piperidino unsubstituted or substituted by hydroxy, alkyl of 1 to 4 carbon atoms, alkoxy of 1 to 4 carbon atoms, or alkyloxycarbonyl in which the alkyl portion contains 1 to 4 carbon atoms; morpholino unsubstituted or substituted by one or two alkyls of 1 to 4 carbon atoms; thiomorpholino; piperazino unsubstituted or substituted on the nitrogen atom by alkyl of 1 to 4 carbon atoms, alkyloxycarbonyl in which the alkyl contains 1 to 4 carbon atoms, acyl of 2 to 5 carbon atoms, or formyl; or a piperazinone ring unsubstituted or substituted on the nitrogen by alkyl of 1 to 4 carbon atoms.

When the groups $R_1$ and $R_2$ contain one or more asymmetric carbon atoms, there are several stereoisomers corresponding to the planar formula (I). These various stereoisomers also form part of the invention.

The compounds of formula (I) can be prepared by the action of an amine of formula:

in which $R_1$ and $R_2$ have the same meanings as in the formula (I), or a salt of this amine, on a derivative of formula:

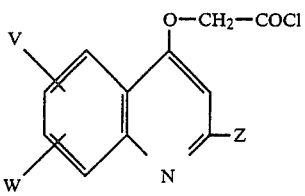

in which V, W and Z have the same meanings as in the formula (I).

As a salt of the amine of formula (II), the hydrochloride or para-toluenesulphonate, for example, may be mentioned.

This reaction can be carried out according to processes, known per se, by means of which a carboxylic acid chloride can be converted to a carboxamide, e.g. those described by C. A. Buehler and D. E. Pearson, Survey of Organic Synthesis, Wiley Interscience, p. 894, 1970.

The acid chloride of formula (III) can be treated with an excess of the amine of formula (II) in an inert solvent such as toluene, chloroform or methylene chloride, at a temperature between 20° C. and the boiling point of the solvent used. The excess of amine used, which performs the role of a base which neutralizes the hydrochloric acid formed in the reaction, is at least one equivalent, i.e. the total amount of amine used is at least two equivalents.

The acid chloride of formula (III) can also be reacted with the amine of formula (II) in the presence of a tertiary amine such as triethylamine, in an inert solvent such as toluene, chloroform or methylene chloride, at a temperature between 20° C. and the boiling point of the solvent. In the case where a salt of an amine of formula (II) is used, it is necessary to use at least 2 equivalents of tertiary amine for one equivalent of amine salt.

In the case where the acid chloride of formula (III) is in the form of a hydrochloride, it is necessary to use one additional equivalent of amine of formula (II) or tertiary amine.

The compounds of formula (III) can be obtained by the action on an acid of formula:

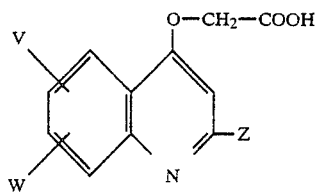

in which V, W and Z have the same meanings as in the formula (III), of a chlorinating agent such as thionyl chloride.

The reaction of the acid of formula (IV) with the chlorinating agent can be carried out in the absence of solvent or in an inert solvent such as chloroform or toluene, preferably at the refluxing temperature of the medium.

The acids of formula (IV) can be obtained by application or adaptation of the methods described in Example 1, and in R. B. Wagner and H. D. Zook, Synthetic Organic Chemistry, J. Wiley, p. 411–478 (1953) and C. A. Buehler and D. E. Pearson, Survey of Organic Synthesis, Wiley Interscience, p. 655–710 (1970).

The compounds of formula (I) in which V and W, which may be identical or different, denote hydrogen, halogen, alkyl of 1 to 4 carbon atoms, alkoxy of 1 to 4 carbon atoms, Z denotes phenyl, thienyl, pyridyl or phenyl substituted by one or two substituents chosen from halogen, alkyl of 1 to 4 carbon atoms, alkoxy of 1 to 4 carbon atoms, trifluoromethyl, and nitro, and $R_1$ and $R_2$ are as defined above, can also be prepared by the action of a compound of formula:

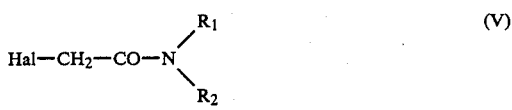

in which $R_1$ and $R_2$ have the same meanings as above and Hal denotes a halogen (chlorine or bromine) atom, on a derivative of formula:

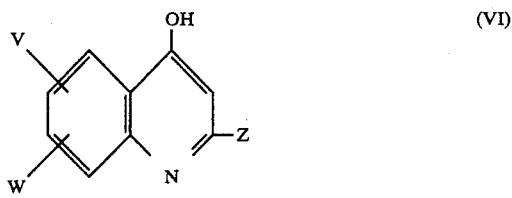

in which V, W and Z have the same meanings as above.

This reaction can be carried out according to known processes, such as that described in Chem. Abst 95, 203 770K (1981), consists in working in the presence of a base such as potassium carbonate, preferably in the presence of cuprous iodide, in a solvent such as 2-butanone and at a temperature between 20° C. and the boiling point of the solvent.

Most of the compounds of formula (VI) are known; the new compounds can be obtained by application or adaptation of the methods described by C. Hauser and A. Reynolds, J.A.C.S., 70, 2402–2404 (1948), A. Kasahara, Chem. Ind. 4, 121 (1981), Sorm, Chem. Listy, 49, 901 (1954), B. Staskun et al., J. Org. Chem., 26, 319 (1961), and Elderfield et al., J. Amer. Chem. Soc., 68, 1272 (1946).

The compounds of formula (I) in which V and W, which may be identical or different, denote hydrogen, halogen, alkyl of 1 to 4 carbon atoms, alkoxy of 1 to 4 carbon atoms, Z denotes phenyl, thienyl, pyridyl or phenyl substituted by one or two substituents chosen from halogen, alkyl of 1 to 4 carbon atoms, alkoxy of 1 to 4 carbon atoms, trifluoromethyl and nitro, and $NR_1R_2$ denotes a piperidine ring substituted by alkoxy of 1 to 4 carbon atoms, can also be prepared by the action of a compound of formula:

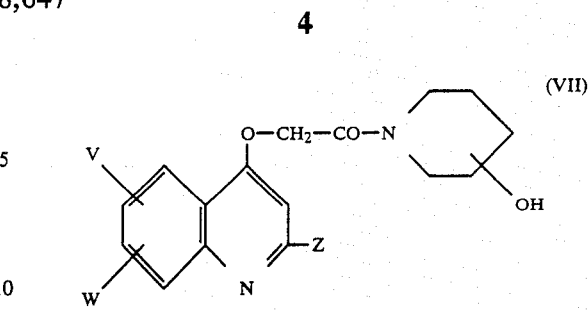

in which V, W and Z have the meanings stated above, on a derivative of formula:

in which Hal denotes a halogen (chlorine or bromine) atom and R denotes alkyl of 1 to 4 carbon atoms.

This reaction is performed in an inert solvent such as tetrahydrofuran, in the presence of a base such as sodium hydride and at the boiling point of the solvent.

The compounds of formula (I) in which V and W, which may be identical or different, denote hydrogen, halogen, alkyl of 1 to 4 carbon atoms, or alkoxy of 1 to 4 carbon atoms, Z denotes a phenyl, thienyl, pyridyl, or phenyl substituted by one or two substituents chosen from halogen, alkyl of 1 to 4 carbon atoms, alkoxy of 1 to 4 carbon atoms, trifluoromethyl, and nitro and $NR_1R_2$ denotes a piperazinone ring substituted on the nitrogen atom by alkyl of 1 to 4 carbon atoms, can also be prepared by alkylation of the corresponding compounds of formula (I), for which $NR_1R_2$ denotes a piperazinone ring, with an alkyl halide of formula (VIII) in which Hal denotes halogen and R denotes alkyl of 1 to 4 carbon atoms.

This reaction can be performed in an inert solvent such as toluene, dimethylformamide or dimethyl sulphoxide, at room temperature, in the presence of a base such as sodium hydride.

The compounds of formula (I) in which V and/or W are amino groups and/or Z is a phenyl radical substituted by one or two amino groups, and $R_1$ and $R_2$ are defined as above, with the proviso that these compounds do not contain nitro groups, can be prepared by reduction of the corresponding nitro derivatives.

This reduction may, for example, be effected by catalytic hydrogenation, e.g. in methanol at a temperature from 20° to 40° C., in the presence of a catalyst such as palladium on charcoal and under a hydrogen pressure of 1 bar.

Alternatively the reduction may be advantageously performed in ethanol using an aqueous sodium dithionite solution, at the boiling point of the solvent.

The compounds of formula (I) in which V and/or W are acylamino of 1 to 4 carbon atoms, and Z, $R_1$ and $R_2$ are as defined above, with the proviso that Z is not phenyl substituted by amino, can be obtained by acylation of the corresponding amino derivatives of formula (I) using an acylating agent of formula:

in which Hal denotes halogen and E denotes hydrogen or alkyl of 1 to 3 carbon atoms.

This reaction is advantageously performed in methylene chloride in the presence of a base such as triethylamine.

The enantiomers of the compounds of formula (I) can be obtained by resolution of the racemates, for example by chromatography on a chiral column according to the method of W. H. Pirkle et al., Asymmetric Synthesis, vol. 1, Academic Press (1983) or alternatively by synthesis from chiral precursors.

The reaction mixtures obtained by the various processes described above are treated according to conventional physical methods (evaporation, extraction, distillation, crystallization, chromatography) or, where appropriate, chemical methods (salt formation and regeneration of the base or acid) in order to isolate the compounds of formula (I) in the pure state.

Where possible, the compounds of formula (I) in the form of the free base can optionally be converted to addition salts with an inorganic or organic acid, by the action of such an acid in an organic solvent such as an alcohol, a ketone, an ether or a chlorinated solvent.

The compounds of formula (I) and their salts possess advantageous pharmacological properties. These compounds bind to cerebral type benzodiazepine receptors, and are consequently useful as anxiolytics.

The affinity of the compounds of formula (I) for cerebral type benzodiazepine receptors was determined according to the method of Mohler et al., Life Sciences, 20, 2101 (1977) on membranes of rat brain, using [³H]diazepam as ligand. This affinity as calculated by the formula:

$$Ki = \frac{IC_{50}}{1 + \frac{C}{KD}}$$

where Ki is the affinity, C is the concentration of [³H]diazepam used, $K_D$ is an affinity constant characteristic of diazepam, and $IC_{50}$ is the concentration of the product under test required to obtain 50% inhibition of the binding of the [³H]diazepam, is between 0.001 and 0.5 uM.

The compounds according to the invention possess low toxicity. Their oral $LD_{50}$ in mice is greater than 200 mg/kg. The $LD_{50}$ values were calculated after 3 days of observation by the cumulative method of J. J. Reed and H. Muench, Amer. J. Hyg., 27, 493 (1938).

The following compounds are of special value:
N-isopropyl-N-methyl-(2-phenyl-4-quinolyl)oxyacetamide
4-{[2-(4-methylphenyl)-4-quinolyl]oxyacetyl}morpholine
4-{[2-2-fluorophenyl)-4-quinolyl]oxyacetyl}morpholine
4-{[2-(2-thienyl)-4-quinolyl]oxyacetyl}morpholine
4-[(2-phenyl-4-quinolyl)oxyacetyl]thiomorpholine
N-cyclopropylmethyl-N-methyl-(2-phenyl-4-quinolyl)-oxyacetamide
4-{[2-(3-chlorophenyl)-4-quinolyl]oxyacetyl}morpholine
2,6-dimethyl-4-[(2-phenyl-4-quinolyl)oxyacetyl]-morpholine
1-[(2-phenyl-4-quinolyl)oxyacetyl]-4-piperidinol
4-[(2-phenyl-4-quinolyl)oxyacetyl]-2-piperazinone
1-formyl-4-[(2-phenyl-4-quinolyl)oxyacetyl]piperazine
4-[(5-chloro-2-phenyl-4-quinolyl)oxyacetyl]morpholine
N-methyl-N-(4-morpholinyl)-(2-phenyl-4-quinolyl)-oxyacetamide
4-[(6-chloro-2-phenyl-4-quinolyl)oxyacetyl]morpholine
1-[(2-phenyl-4-quinolyl)oxyacetyl]pyrrolidine
N,N-diethyl-(2-phenyl-4-quinolyl)oxyacetamide
1-[(2-phenyl-4-quinolyl)oxyacetyl]piperidine
4-[(2-phenyl-4-quinolyl)oxyacetyl]morpholine
N-methyl-N-(1-methylpropyl)-(2-phenyl-4-quinolyl)-oxyacetamide
4-{[2-(4-chlorophenyl)-4-quinolyl]oxyacetyl}morpholine
4-[(6-methyl-2-phenyl-4-quinolyl)oxyacetyl]morpholine
3-methyl-1-[(2-phenyl-4-quinolyl)oxyacetyl]piperidine
4-[(6-acetylamino-2-phenyl-4-quinolyl)oxyacetyl]-morpholine
4-{[2-(4-aminophenyl)-4-quinolyl]oxyacetyl}morpholine
4-{[2-(3-thienyl)-4-quinolyl]oxyacetyl}morpholine
N-cyclobutyl-N-methyl-(2-phenyl-4-quinolyl)oxyacetamide.

For medicinal use, it is possible to use the products of formula (I) as they are or, when they can exist, as salts with pharmaceutically acceptable strong acids.

As pharmaceutically acceptable salts, there may be mentioned the addition salts with inorganic acids, e.g. hydrochlorides, sulphates, nitrates or phosphates, or organic acids, e.g. acetates, propionates, succinates, benzoates, fumarates, theophyllineacetates, salicylates or methylenebis(β-hydroxynaphthoates), or substitution derivatives of these products.

The examples which follow show how the invention may be put into practice.

EXAMPLE 1

(2-Phenyl-4-quinolyl)oxyacetic acid (3.5 g) and thionyl chloride (2.8 cc) in chloroform (300 cc) are heated under reflux for 8 hours 30 minutes. The solvents are removed under reduced pressure, and the residue obtained is added, in the course of 15 minutes, to a solution, cooled beforehand to 5° C., of diethylamine (13 cc) in methylene chloride (100 cc). The mixture is stirred for 1 hour 30 minutes at 5°–10° C., and the organic phase is washed with water (6×100 cc), dried over magnesium sulphate and evaporated under reduced pressure. The residue obtained is chromatographed on silica gel using a cyclohexane/ethyl acetate (80–20 by volume) mixture as eluant.

The residue obtained is recrystallized in an isopropyl ether/acetonitrile (10:1 by volume) mixture. N,N-Diethyl-[(2-phenyl-4-quinolyl)oxy]acetamide (1.91 g, m.p. 97° C.), is thereby isolated.

(2-Phenyl-4-quinolyl)oxyacetic acid can be prepared by saponification of the corresponding ethyl ester using normal sodium hydroxide solution. Its m.p. is 179°–181° C.

Ethyl (2-phenyl-4-quinolyl)oxyacetate can be prepared in the following manner:

Ethyl bromoacetate (4.4 cc) is added dropwise to a stirred suspension of 2-phenyl-4-quinolinol (8.8 g) and potassium carbonate (11 g) in methyl ethyl ketone (300 cc).

The mixture is heated under reflux for 3 hours. The mixture is brought back to room temperature (approximately 20° C.), the insoluble material is drained and the solvents are removed under reduced pressure.

The residue is taken up with 40°–70° petroleum ether (100 cc) and the mixture is filtered. Ethyl (2-phenyl-4-quinolyl)oxyacetate (11.1 g), m.p. 96° C., is thereby isolated.

2-Phenyl-4-quinolinol can be prepared according to C. Hauser and A. Reynolds, J.A.C.S. 70, 2402 (1948).

EXAMPLE 2

The procedure is as in Example 1, but starting with (2-phenyl-4-quinolyl)oxyacetic acid (3 g), thionyl chloride (2.35 cc) in chloroform (50 cc), piperidine (1.04 cc) and triethylamine (3 cc) in toluene (50 cc). The residue obtained is converted in acetone to its hydrochloride by adding a solution of hydrochloric acid in ethyl ether. After recrystallization in ethanol, 1-[(2-phenyl-4-quinolyl)oxyacetyl]piperidine hydrochloride (0.46 g), m.p. 146° C., is obtained.

EXAMPLE 3

The procedure is as in Example 1, but starting with (2-phenyl-4-quinolyl)oxyacetic acid (3 g), thionyl chloride (2.35 cc) in chloroform (80 cc), N-methylpiperazine (1.18 cc) and triethylamine (3 cc) in toluene (50 cc).

The residue obtained is taken up in acetone and, after addition of a solution of hydrochloric acid in ethyl ether, 4-methyl-1-[(2-phenyl-4-quinolyl)oxyacetyl]piperazine dihydrochloride (1.1 g), m.p. 182° C., is isolated.

EXAMPLE 4

The procedure is as in Example 1, but starting with (2-phenyl-4-quinolyl)oxyacetic acid (3 g), thionyl chloride (3.12 cc) in chloroform (100 cc), morpholine (0.94 cc) and triethylamine (3 cc) in toluene (50 cc).

The residue obtained is recrystallized twice in ethyl acetate.4-[(2-Phenyl-4-quinolyl)oxyacetyl]morpholine (1.43 g), m.p. 145° C., is thereby obtained.

EXAMPLE 5

A solution of 4-(2-bromoacetyl)morpholine (2.94 g) in methyl ethyl ketone (40 cc) is added to a stirred suspension of 2-(4-chlorophenyl)-4-hydroxyquinoline (3.5 g) and anhydrous potassium carbonate (3.74 g) in 2-butanone (200 cc).

The mixture is heated under reflux for 15 hours and cooled to room temperature (approximately 20° C.), the insoluble material is removed by filtration and the methyl ethyl ketone evaporated under reduced pressure.

After recrystallization of the residue in an isopropyl ether/ethyl acetate (10:1 by volume) mixture, 4-{[2-(4-chlorophenyl)-4-quinolyl]oxyacetyl}morpholine (1.6 g) is isolated and this is converted in acetone to its hydrochloride by adding a solution of hydrochloric acid in ethyl ether. This hydrochloride has an m.p. of 191° C.

2-(4-Chlorophenyl)-4-hydroxyquinoline can be prepared according to Kasahara et al., Chem. Ind. (London) (4), 121 (1981).

EXAMPLE 6

The procedure is as in Example 1, but starting with (2-phenyl-4-quinolyl)oxyacetic acid (3 g), thionyl chloride (3.12 cc) in triethylamine (100 cc), N-methyl-2-butanamine (1.39 g) and triethylamine (3 cc) in toluene (50 cc) on a sieve. The residue obtained is taken up in acetone and, after addition of a solution of hydrochloric acid in ethyl ether and two recrystallizations, the first is an ethanol/ethyl ether mixture and the second is isopropanol, N-methyl-N-(1-methylpropyl)-(2-phenyl-4-quinolyl)oxyacetamide hydrochloride (0.69 g), m.p. 172° C., is isolated.

EXAMPLE 7

The procedure is as in Example 5, starting with 2-(4-methoxyphenyl)-4-hydroxyguinoline (3 g), 4-(2-bromoacetyl)morpholine (2.6 g) and potassium carbonate (3.3 g) in methyl ethyl ketone (100 cc). After chromatography of the residue on silica gel using ethyl acetate as eluant, the product obtained is taken up in acetone and, after addition of a solution of hydrochloric acid in ethyl ether, 4-{[2-(4-methoxyphenyl)-4-quinolyl]oxyacetyl}morpholine hydrochloride (1.2 g), m.p. 215° C., is isolated.

2-(4-Methoxyphenyl)-4-hydroxyquinoline can be prepared according to Sorm, Chem. Listy 49, 901 (1954).

EXAMPLE 8

(2-Phenyl-4-quinolyl)oxyacetic acid (1.8 g) and thionyl chloride (1.41 cc) in chloroform (54 cc) are heated under reflux for 3 hours. The solvent is removed under reduced pressure and the residue obtained is suspended in chloroform (40 cc).

N-Methylbenzylamine (0.83 cc) and triethylamine (2 cc) in chloroform (10 cc) are added slowly with stirring to this suspension, the temperature being maintained at 10° C. The mixture is stirred for 15 minutes at room temperature (approximately 20° C.), the solvent evaporated under reduced pressure and the residue taken up with ethyl acetate (50 cc) and water (20 cc). The organic phase is decanted and washed with water (2×10 cc), then with normal hydrochloric acid solution (10 cc) and finally with water (10 cc).

After evaporation of the solvent under reduced pressure, the residue is dissolved in acetonitrile and crystallized by slow addition of isopropyl ether. After recrystallization of the crude product in an acetonitrile/isopropyl ether mixture, N-benzyl-N-methyl-(2-phenyl-4-quinolyl)oxyacetamide (0.85 g), m.p. 102° C., is isolated.

EXAMPLE 9

The procedure is as in Example 1, starting with (2-phenyl-4-quinolyl)oxyacetic acid (6 g), thionyl chloride (4.6 cc) in chloroform (180 cc), ethyl 1-piperazinecarboxylate (3.31 g) and triethylamine (6.5 cc) in chloroform (200 cc).

After recrystallization of the residue in an ethyl acetate/ethanol (5:1 by volume) mixture, ethyl 4-[(2-phenyl-4-quinolyl)oxyacetyl]-1-piperazinecarboxylate (3 g), m.p. 163° C., is isolated.

EXAMPLE 10

The procedure is as in Example 1, starting with (2-phenyl-4-quinolyl)oxyacetic acid (2 g), thionyl chloride (1.5 cc) in chloroform (70 cc), thiomorpholine (0.71 g) and triethylamine (2.1 cc) in chloroform (70 cc).

After dissolution in ethyl acetate and crystallization by adding isopropyl ether, 4-[(2-phenyl-4-quinolyl)oxyacetyl]thiomorpholine (1.8 g), m.p. 130° C., is isolated.

EXAMPLE 11

The procedure is as in Example 1, starting with (4-chloro-2-phenyl-4-quinolyl)oxyacetic acid (2.2 g), thionyl chloride (1.5 cc) in chloroform (70 cc), thiomorpholine (0.71 g) and triethylamine (2.1 cc) in chloroform (70 cc).

After recrystallization in ethyl acetate, 4-{[2-(4-chlorophenyl)-4-quinolyl]oxyacetyl}thiomorpholine (0.8 g), m.p. 117° C., is isolated.

(4-Chloro-2-phenyl-4-quinolyl)oxyacetic acid is prepared in the same manner as (2-phenyl-4-quinolyl)oxyacetic acid described in Example 1. Its m.p. is 230° C. with decomposition.

EXAMPLE 12

The procedure is as in Example 5, starting with 6-methoxy-2-phenyl-4-quinolinol (3 g), 4-(2-bromoacetyl)morpholine (2.3 g) and potassium carbonate (3.3 g) in methyl ethyl ketone (100 cc), reducing the reaction time to 6 hours.

The residue is converted in an ethyl ether/acetone (5:1 by volume) mixture to a crude hydrochloride by adding a solution of hydrochloric acid in isopropanol. This hydrochloride is taken up hot in an acetone/water mixture. After filtration and drying, 4-[(6-methoxy-2-phenyl-4-quinolyl)oxyacetyl]morpholine hydrochloride (2.2 g), m.p. 179° C., is obtained.

6-Methoxy-2-phenyl-4-quinolinol can be prepared according to B. Staskun and S. S. Israelstam, J. Org. Chem., (26), p. 3191 (1961).

EXAMPLE 13

The procedure is as in Example 1, starting with (2-phenyl-4-quinolyl)oxyacetic acid (3 g), thionyl chloride (3.8 cc) in chloroform (90 cc) and a 3M solution (12.5 cc) of dimethylamine in toluene, reducing the time of preparation of the acid chloride to 3 hours.

After recrystallization of the residue is a toluene/isopropyl ether mixture, N,N-dimethyl-(2-phenyl-4-quinolyl)oxyacetamide (2.2 g), m.p. 112° C., is isolated.

EXAMPLE 14

The procedure is as in Example 1, starting with (2-phenyl-4-quinolyl)oxyacetic acid (3 g), thionyl chloride (3.8 cc) in chloroform (90 cc) and N-methylisopropylamine (2.7 cc) in chloroform (90 cc), reducing the time of preparation of the acid chloride to three hours.

After chromatography of the residue on silica gel using a cyclohexane/ethyl acetate (50:50 by volume) mixture as eluant, and recrystallization in isopropyl ether, N-methyl-N-isopropyl-(2-phenyl-4-quinolyl)oxyacetamide (1.3 g), m.p. 80° C., is isolated.

EXAMPLE 15

The procedure is as in Example 1, starting with (2-phenyl-4-quinolyl)oxyacetic acid (3 g), thionyl chloride (3.8 cc) in chloroform (90 cc) and 2,6-dimethylmorpholine (1.32 cc) and triethylamine (3.25 cc) in chloroform (90 cc), reducing the time of preparation of the acid chloride to 3 hours.

After chromatography of the residue of silica gel using a cyclohexane/ethyl acetate mixture as eluant, and recrystallization in isopropyl ether, 2,6-dimethyl-4-[(2-phenyl-4-quinolyl)oxyacetyl]morpholine (1.7 g), m.p. 117° C., is isolated.

EXAMPLE 16

The procedure is as in Example 1, starting with (2-phenyl-4-quinolyl)oxyacetic acid (3 g), thionyl chloride (3.8 cc) in chloroform (90 cc) and 4-hydroxypiperidine (1.08 g) and triethylamine (3.25 cc) in chloroform (90 cc), reducing the time of preparation of the acid chloride to 3 hours.

The residue was taken up in ethanol and, after addition of a solution of hydrochloric acid in ethyl ether, 1-[(2-phenyl-4-quinolyl)oxyacetyl]-4-piperidinol hydrochloride (3 g), m.p. 185° C., is isolated.

EXAMPLE 17

The procedure is as in Example 1, starting with (2-phenyl-4-quinolyl)oxyacetic acid (3 g), thionyl chloride (3.8 cc) in chloroform (90 cc), N-methyl-2-methoxyethylamine hydrochloride (1.34 g) and triethylamine (4.5 cc) in chloroform (90 cc), reducing the time of preparation of the acid chloride to 3 hours.

After two recrystallizations in an ethyl acetate/isopropyl ether mixture, N-methyl-N-(2-methoxyethyl)-(2-phenyl-4-quinolyl)oxyacetamide (1.6 g), m.p. 109° C., is isolated.

N-Methyl-2-methoxyethylamine can be prepared according to Mndshojan et al., Doklady Akad. Armjansk, SSR 27 (1958). 161, 167.

EXAMPLE 18

The procedure is as in Example 1, starting with (2-phenyl-4-quinolyl)oxyacetic acid (3 g), thionyl chloride (3.8 cc) in chloroform (90 cc), 1-acetylpiperazine paratoluenesulphonate (3.2 g) and triethylamine (4.5 cc) in chloroform (90 cc), reducing the time of preparation of the acid chloride to 3 hours.

After chromatography of the residue on silica gel using an ethyl acetate/chloroform/ethanol (70:20:10 by volume) mixture as eluant, and recrystallization in an ethanol/isopropyl ether mixture, 1-acetyl-4-[2-phenyl-4-quinolyl)oxyacetyl]piperazine (1 g), m.p. 184° C., is isolated.

1-Acetylpiperazine para-toluenesulphonate can be prepared according to H. K. Hall, J. Am. Chem. Soc., (78), 2570, (1956).

EXAMPLE 19

The procedure is as in Example 1, starting with (2-phenyl-4-quinolyl)oxyacetic acid (3 g), thionyl chloride (3.8 cc) in chloroform (90 cc), 2-piperazinone (1.07 g) and triethylamine (3.25 cc) in chloroform (90 cc), reducing the time of preparation of the acid chloride to 3 hours.

When the reaction is complete, the precipitate is drained, washed with water then with decinormal sodium hydroxide solution and then with water again; the precipitate is recrystallized in acetic acid.

4-[(2-Phenyl-4-quinolyl)oxyacetyl]-2-piperazinone (1.9 g), m.p. 215° C., is thereby obtained.

2-Piperazinone can be prepared according to S. R. Aspinall, J. Am. Chem. Soc. (62), 1202 (1940).

EXAMPLE 20

1-[(2-Phenyl-4-quinolyl)oxyacetyl]-4-piperidinol (3.8 g), prepared according to Example 16, in dry tetrahydrofuran (80 cc) is placed under an atmosphere of nitrogen.

Sodium hydride (0.42 g), in a 60% strength dispersion to oil, is added gradually, and the mixture is then stirred for two hours at room temperature (approximately 20° C.). The mixture is then heated to reflux and methyl iodide (1.37 cc) in tetrahydrofuran (10 cc) is allowed to run in slowly in the course of 30 minutes. The mixture is heated under reflux for one hour, methyl iodide (1.37 cc) in tetrahydrofuran (100 cc) is added again and the mixture is heated under reflux for 30 minutes and cooled to room temperature, sodium hydride (0.21 g), in a 60% strength dispersion in oil, is added and the mixture is then heated under reflux for 30 minutes. The dual addition of methyl iodide and sodium hydride is repeated twice under the conditions described above.

The solvent is evaporated off under reduced pressure and the residue taken up with water (150 cc) and ethyl acetate (100 cc). The organic phase is washed with water, dried over magnesium sulphate and evaporated under reduced pressure.

The residue is chromatographed on silica gel using ethyl acetate as eluant, and then recrystallized in an ethyl acetate/isopropyl ether (1:8 by volume) mixture. 4-Methoxy-1-[(2-phenyl-4-quinolyl)oxyacetyl]piperidine (1.7 g), m.p. 96° C., is thereby obtained.

EXAMPLE 21

The procedure is as in Example 1, starting with (2-phenyl-4-quinolyl)oxyacetic acid (3 g), thionyl chloride (3.8 cc) in chloroform (90 cc), 4-(methylamino)morpholine (1.25 g) and triethylamine (3.25 cc) in chloroform (90 cc).

After recrystallization of the residue in acetonitrile, N-methyl-N-(4-morpholinyl)-(2-phenyl-4-quinolyl)oxyacetamide (2 g), m.p. 189° C., is isolated.

4-(Methylamino)morpholine can be prepared according to O. Zinngr, H. Boehlke and W. Kliegel, Arch. Pharm. 299, 245–53 (1966).

EXAMPLE 22

The procedure is as in Example 1, starting with (2-phenyl-4-quinolyl)oxyacetic acid (3 g), thionyl chloride (3.8 cc) in chloroform (90 cc), (cyclopropylmethyl)methylamine hydrochloride (1.3 g) and triethylamine (4.4 cc) in chloroform (90 cc).

The residue is chromatographed on silica gel using a cyclohexane/ethyl acetate (50:50 by volume) mixture as eluant.

The residue is taken up in acetone and, after addition of a solution of hydrochloric acid in ethyl ether, N-cyclopropylmethyl-N-methyl-(2-phenyl-4-quinolyl)oxyacetamide hydrochloride (1.6 g), m.p. 178° C., is isolated.

EXAMPLE 23

The procedure is as in Example 5, starting with 2-(4-methylphenyl)-4-hydroxyquinoline (6 g) in methyl ethyl ketone (200 cc), anhydrous potassium carbonate (7.05 g) and 4-(2-bromoacetyl)morpholine (5.84 g) in methyl ethyl ketone (40 cc).

After recrystallization of the residue in ethyl acetate, 4-{[2-(4-methylphenyl)-4-quinolyl]oxyacetyl}morpholine (4.65 g), m.p. 146° C., is obtained.

2-(4-Methylphenyl)-4-hydroxyquinoline can be prepared by the action of ethyl 4-methylbenzoylacetate (0.294 mole) on aniline (0.294 mole) at 140° C. in the presence of polyphosphoric acid (168 g). Its m.p. is above 268° C.

EXAMPLE 24

The procedure is as in Example 5, starting with 2-(3-trifluoromethylphenyl)-4-hydroxyquinoline (2.3 g) in methyl ethyl ketone (75 cc), potassium carbonate (2.2 g) and 4-(2-bromoacetyl)morpholine (1.85 g) in methyl ethyl ketone (15 cc).

After two successive chromatographic separations of the residue on silica gel, the first using ethyl acetate and the second using a cyclohexane/ethyl acetate (30:50 by volume) mixture is eluant, 4-{[2-(3-trifluoromethylphenyl)-4-quinolyl]oxyacetyl}morpholine (1.05 g), m.p. 135° C., is isolated.

2-(3-Trifluoromethylphenyl)-4-hydroxyquinoline can be prepared by the action of ethyl 3-trifluoromethylbenzoylacetate (0.245 mole) on aniline (0.245 mole) at 160° C. in the presence of polyphosphoric acid (156 g). This product is used as it is in the following stage.

EXAMPLE 25

The procedure is as in Example 5, starting with 2-(2-fluorophenyl)-4-hydroxyquinoline (4.1 g) in methyl ethyl ketone (130 cc), anhydrous potassium carbonate (4.8 g) and 4-(2-bromoacetyl)morpholine (3.95 g) in methyl ethyl ketone (25 cc).

After crystallization of the residue in 40°-60° petroleum ether followed by recrystallization in ethyl acetate, 4-{[2-(2-fluorophenyl)-4-quinolyl]oxyacetyl}morpholine (2.5 g), m.p. 145° C., is isolated.

2-(2-Fluorophenyl)-4-hydroxyquinoline can be prepared by the action of ethyl 2-fluorobenzoylacetate (0.05 mole) on aniline (0.05 mole) at 160° C. in the presence of polyphosphoric acid (25 g).

Its m.p. is 224° C.

EXAMPLE 26

The procedure is as in Example 5, starting with 2-(2-thienyl)-4-hydroxyquinoline (3.4 g) in methyl ethyl ketone (110 cc), anhydrous potassium carbonate (4.15 g) and 4-(2-bromoacetyl)morpholine (3.45 g) in methyl ethyl ketone (20 cc).

The residue is taken up in ethyl ether and, after addition of a solution of hydrochloric acid in isopropanol, a crude hydrochloride is isolated. The latter is taken up with water (100 cc), methylene chloride (100 cc) and normal sodium hydroxide solution (30 cc). The organic phase is decanted, washed with water, dried over magnesium sulphate and evaporated under reduced pressure. The residue is stirred for 15 minutes in ethyl ether. After filtration and drying, 4-{[2-(2-thienyl)-4-quinolyl]oxyacetyl}morpholine (2.15 g), m.p. 198° C., is isolated.

2-(2-Thienyl)-4-hydroxyquinoline can be prepared by the action of ethyl 2-thenoylacetate (0.103 mole) on aniline (0.103 mole) at 160° C. in the presence of polyphosphoric acid (45.8 g). Its m.p. is a above 268° C.

EXAMPLE 27

The procedure is as in Example 5, starting with 2-(3-chlorophenyl)-4-hydroxyquinoline (1.9 g) in methyl ethyl ketone (50 cc), potassium carbonate (2.05 g) and 4-(2-bromoacetyl)morpholine (1.7 g) in methyl ethyl ketone (10 cc).

After chromatography of the residue on silica gel using a cyclohexane/ethyl acetate (50:50 by volume) mixture as eluant, and crystallization in 40°-60° petroleum ether, 4-{[2-(3-chlorophenyl)-4-quinolyl]oxyacetyl}morpholine (1.4 g), m.p. 131° C., is isolated.

2-(3-Chlorophenyl)-4-hydroxyquinoline can be prepared by the action of ethyl 3-chlorobenzoylacetate (0.025 mole) on aniline (0.025 mole) at 160° C. in the presence of polyphosphoric acid (11 g).

Its m.p. is 210° C.

EXAMPLE 28

The procedure is as in Example 5, starting with 2-(2-pyridyl)-4-hydroxyquinoline (2.22 g) in methyl ethyl ketone (70 cc), anhydrous potassium carbonate (2.76 g) and 4-(2-bromoacetyl)morpholine (2.3 g) in methyl ethyl ketone (15 cc).

After chromatography of the residue on silica gel using a methanol/ethyl acetate (50:50 by volume) mixture as eluant, the solid obtained is recrystallized in ethyl acetate. 4-{[2-(2-Pyridyl)-4-quinolyl]oxyacetyl}morpholine (1.8 g), m.p. 185° C., is thereby isolated.

2-(2-Pyridyl)-4-hydroxyquinoline can be prepared by the action of ethyl (2-pyridinecarbonyl)acetate (0.05 mole) on aniline (0.05 mole) at 160° C. in the presence of polyphosphoric acid (58 g).

Its m.p. is 228° C.

EXAMPLE 29

Dimethyl sulphoxide (20 cc) and then sodium hydride (0.73 g), in a 60% strength dispersion in oil, are added to a suspension of 4-[(2-phenyl-4-quinolyl)-oxyacetyl]-2-piperazinone (6 g), prepared according to Example 19, in toluene (120 cc) and dimethylformamide (50 cc).

The mixture is stirred for 3 hours 30 minutes at room temperature (approximately 20° C.), methyl iodide (1.13 cc) is added and the mixture is then stirred for 40 hours at room temperature. Water (200 cc) is then added and the mixture is extracted with ethyl acetate (3×150 cc). The organic phase is washed with water, dried over magnesium sulphate and evaporated under reduced pressure. The residue is chromatographed on silica gel using an ethyl acetate/ethanol (95:5 by volume) mixture is eluant. 1-Methyl-4-[(2-phenyl-4-quinolyl)oxyacetyl]-2-piperazinone (3.5 g), m.p. 140° C., is thereby isolated.

EXAMPLE 30

The procedure is as in Example 1, starting with (2-phenyl-4-quinolyl)oxyacetic acid (6 g), thionyl chloride (4.6 cc) in chloroform (180 cc), 1-formylpiperazine (2.4 g) and triethylamine (6.5 cc) in chloroform (200 cc).

After two recrystallizations, the first in ethyl acetate and the second in ethanol, 1-formyl-4-[(2-phenyl-4-quinolyl)oxyacetyl]piperazine (2.6 g), m.p. 170° C., is isolated.

EXAMPLE 31

The procedure is as in Example 5, starting with 2-(4-nitrophenyl)-4-hydroxyquinoline (5.32 g) in methyl ethyl ketone (165 cc), anhydrous potassium carbonate (5.5 g) and 4-(2-bromoacetyl)morpholine (4.6 g) in methyl ethyl ketone (32 cc).

After chromatography of the residue on silica gel using a cyclohexane/ethyl acetate (30:70 by volume) mixture as eluant, a solid is isolated and this is stirred in 40°–60° C. petroleum ether. 4-{[2-(4-Nitrophenyl)-4-quinolyl]oxyacetyl}morpholine (4.8 g), m.p. 172° C., is isolated.

2-(4-Nitrophenyl)-4-hydroxyquinoline can be prepared according to Elderfield et al., J. Amer. Chem. Soc., 68, 1272 (1946).

EXAMPLE 32

The procedure is as in Example 5, starting with a 50:50 (by weight) mixture (6 g) of 5-chloro-2-phenyl-4-quinolinol and 7-chloro-2-phenyl-4-quinolinol, 4-(2-bromoacetyl)morpholine (4.88 g) and potassium carbonate (6.3 g) in methyl ethyl ketone (200 cc).

After chromatography of the residue on silica gel using a chloroform/ethyl acetate (50:50 by volume) mixture, a residue is isolated and this is recrystallized in ethyl acetate. 4-[(5-Chloro-2-phenyl-4-quinolyl)oxyacetyl]morpholine (1.8 g), m.p. 168° C., is thereby obtained.

The mixture of 5-chloro-2-phenyl-4-quinolinol and 7-chloro-2-phenyl-4-quinolinol can be obtained by the action of 3-chloroaniline (13 g) on ethyl benzoylacetate (19.8 g) in the presence of polyphosphoric acid (70 g).

EXAMPLE 33

The procedure is as in Example 5, starting with 6-chloro-2-phenyl-4-quinolinol (3 g), 4-(2-bromoacetyl)-morpholine (2.5 g) and potassium carbonate (3.2 g) in methyl ethyl ketone (100 cc).

After recrystallization of the residue in ethyl acetate, 4-[(6-chloro-2-phenyl-4-quinolyl)oxyacetyl]morpholine (2.9 g), m.p. 182° C., is isolated.

6-Chloro-2-phenyl-4-quinolinol can be prepared according to B. Staskun et al., J. Org. Chem. 1961, (26), 3191.

EXAMPLE 34

The procedure is as in Example 1, starting with (2-phenyl-4-quinolyl)oxyacetic acid (6 g), thionyl chloride (4.57 cc) in chloroform (150 cc), pyrrolidine (1.53 g) and triethylamine (6 cc) in chloroform (150 cc), reducing the time of preparation of the acid chloride to three hours.

After recrystallization of the residue in ethyl acetate, 1-[(2-phenyl-4-quinolyl)oxyacetyl]pyrrolidine (5.3 g), m.p. 135° C., is isolated.

EXAMPLE 35

The procedure is as in Example 1, starting with (2-phenyl-4-quinolyl)oxyacetic acid (6 g), thionyl chloride (4.57 cc) in chloroform (150 cc), N-methylaniline (2.3 g) and triethylamine (6 cc) in chloroform (100 cc), reducing the time of preparation of the acid chloride to three hours.

After recrystallization of the residue in ethyl acetate, N-methyl-N-phenyl-(2-phenyl-4-quinolyl)oxyacetamide (5.4 q), m.p. 150° C., is obtained.

EXAMPLE 36

The procedure is as in Example 5, starting with 6-methyl-2-phenyl-4-hydroxyquinoline (3 g), 4-(2-bromoacetyl)morpholine (2.4 g) and potassium carbonate (3.5 g) in methyl ethyl ketone (100 cc).

After recrystallization of the residue in ethyl acetate, 4-[(6-methyl-2-phenyl-4-quinolyl)oxyacetyl]morpholine (2.9 g), m.p. 158° C., is obtained.

6-Methyl-2-phenyl-4-quinolinol can be prepared according to B. Staskun et al., J. Org. Chem. 1961, (26), 3191.

EXAMPLE 37

The procedure is as in Example 1, starting with (2-phenyl-4-quinolyl)oxyacetic acid (6 g), thionyl chloride (4.57 cc) in chloroform (180 cc), 3-methylpiperidine (2 g) and triethylamine (6.48 cc) in chloroform (200 cc), reducing the time of preparation of the acid chloride to 3 hours.

After chromatography of the residue on silica gel using ethyl acetate as eluant, 3-methyl-1-[(2-phenyl-4-quinolyl)-oxyacetyl]piperidine (4.25 g), m.p. 96° C., is isolated.

EXAMPLE 38

The procedure is as in Example 1, starting with (2-phenyl-4-quinolyl)oxyacetic acid (6 g), thionyl chloride (4.57 cc) in chloroform (180 cc), ethyl isonipecotate (3.21 g) and triethylamine (6.5 cc) in chloroform (200 cc), reducing the time of preparation of the acid chloride to 3 hours.

After chromatography of the residue on silica gel using ethyl acetate as eluant, ethyl 1-[(2-phenyl-4- quinolyl)oxyacetyl]-4-piperidinecarboxylate (5.5 g), m.p. 120° C., is isolated.

EXAMPLE 39

4-[(6-Nitro-2-phenyl-4-quinolyl)oxyacetyl]morpholine (12.5 g) in ethanol (550 cc) is heated under reflux for 10 minutes and a solution of sodium dithionite (27.7 g) in water (277 cc) is added in the course of 25 minutes. The mixture is cooled to room temperature (approximately 20° C.) and the ethanol removed under reduced pressure. The aqueous phase is stirred with ethyl acetate and the organic phase is washed with water, dried over magnesium sulphate and evaporated under reduced pressure. The residue obtained is taken up in ethyl ether and converted to the crude hydrochloride by adding a solution of hydrochloric acid in isopropanol. The hydrochloride is taken up with ethyl acetate and aqueous sodium carbonate solution. The precipitate which separates is filtered, heated for 25 minutes in refluxing ethyl acetate, filtered off and dried. 4-[(6-Amino-2-phenyl-4-quinolyl)oxyacetyl]morpholine (1.15 g), m.p. 194° C., is thereby isolated.

4-[(6-Nitro-2-phenyl-4-quinolyl)oxyacetyl]morpholine can be prepared by the process described in Example 5, starting with 6-nitro-2-phenyl-4-hydroxyquinoline (0.133 mole), potassium carbonate (0.265 mole) and 4-(bromoacetyl)morpholine (0.146 mole) in methyl ethyl ketone. Its m.p. is 250° C.

EXAMPLE 40

A solution of acetyl chloride (0.55 cc) in methylene chloride (5 cc) is added in the course of 10 minutes to a stirred solution of 4-[(6-amino-2-phenyl-4-quinolyl)oxyacetyl]morpholine (2.55 g), prepared according to Example 39, and triethylamine (1.2 cc) in methylene chloride (25 cc). The mixture is stirred for 1 hour at room temperature (approximately 20° C.) and the solvent evaporated off under reduced pressure. The residue is stirred for 10 minutes in an ethyl acetate/water (5:2 by volume) mixture, filtered off, dissolved in a toluene/acetic acid (50:50 by volume) mixture and precipitated with ethyl ether. After filtration and drying, 4-[(6-acetylamino-2-phenyl-4-quinolyl)oxyacetyl]morpholine (2 g), m.p. 261° C., is isolated.

EXAMPLE 41

4-{[2-(4-Nitrophenyl)-4-quinolyl]oxyacetyl}morpholine (3.93 g), prepared according to Example 31, dissolved in methanol (80 cc) is hydrogenated at 40° C. for 30 minutes and then at room temperature (approximately 20° C.) and under atmospheric pressure in the presence of a 5N solution (4 cc) of hydrochloric acid in isopropanol and palladinized charcoal (10% Pd) (0.4 g) as catalyst. After absorption of the theoretical amount of hydrogen, normal sodium hydroxide solution (25 cc) is added to the reaction mixture in order to redissolve the precipitate formed. After filtration, the solvent is removed under reduced pressure and the residual aqueous phase is taken up with methylene chloride. The organic phase is washed with water, dried over magnesium sulphate and evaporated under reduced pressure. The residue (2.9 g) is dissolved in hot ethyl acetate (15 cc); ethyl ether (30 cc) is then added, and the precipitate is filtered off and chromatographed on silica gel using a toluene/methanol/diethylamine (90:5:5 by volume) mixture. 4-{[2-(4-Aminophenyl)-4-quinolyl]oxyacetyl}morpholine (1.05 g), m.p. 174° C., is thereby isolated.

EXAMPLE 42

The procedure is as in Example 5, starting with 2-(3-thienyl)-4-hydroxyquinoline (2.85 g) in methyl ethyl ketone (90 cc), potassium carbonate (3.5 g) and 4-(2-bromoacetyl)morpholine (2.9 g) in methyl ethyl ketone (18 cc).

After two recrystallizations of the residue, the first in ethyl acetate and the second in ethanol, 4-{[2-(3-thienyl)-4-quinolyl]oxyacetyl}morpholine (1.7 g), m.p. 183° C., is isolated.

2-(3-Thienyl)-4-hydroxyquinoline can be prepared by the method described by Bogdanowcz et al, Roczniki Chemii, 48, 1255 (1974), starting with ethyl 3-thenoylacetate, aniline and polyphosphoric acid. Its m.p. is above 264° C.

EXAMPLE 43

The procedure is as in Example 5, starting with 2-phenyl-4-hydroxyquinoline (1.6 g) in methyl ethyl ketone (50 cc), potassium carbonate (2 g) and N-methyl-N-tert-butyl-2-bromoacetamide (1.65 g) in methyl ethyl ketone (10 cc).

The residue is converted to a crude hydrochloride by adding a solution of hydrochloric acid in isopropanol. The base is regenerated by adding potassium carbonate solution and extracted with ethyl acetate. The organic phase is washed with water, dried over magnesium sulphate and evaporated under reduced pressure. The residue is crystallized in petroleum ether. N-Methyl-N-tert-butyl(2-phenyl-4-quinolyl)oxyacetamide (1.65 g), m.p. 90° C., is thereby isolated.

N-Methyl-N-tert-butyl-2-bromoacetamide can be prepared by the action of bromoacetyl chloride (0.02 mole) on N-tert-butylmethylamine (0.02 mole) in the presence of triethylamine (0.022 mole) in methylene chloride.

EXAMPLE 44

The procedure is as in Example 1, starting with (2-phenyl-4-quinolyl)oxyacetic acid (19.7 g), thionyl chloride (15.45 cc) in toluene (100 cc), N-methylcyclobutylamine (6 g) and triethylamine (60 cc) in toluene (200 cc), reducing the time of preparation of the acid chloride to two hours.

After chromatography of the residue on silica gel using a cyclohexane/ethyl acetate (70:30 by volume) mixture as eluant, a residue is obtained which is taken up in 40°-60° petroleum ether. After filtration and drying, N-cyclobutyl-N-methyl-(2-phenyl-4-quinolyl)oxyacetamide (12.65 g), m.p. 110° C., is obtained.

N-Methylcyclobutylamine can be prepared by adaptation of the method described by S. F. Blicke et al, J. Amer. Chem. Soc. (74), 3933-34 (1952).

The invention includes within its scope pharmaceutical compositions comprising a compound of formula (I), a mixture of stereoisomeric compounds of formula (I) or, where it can exist, the salt of such a compound or mixture, and one or more diluents or adjuvants which are compatible and pharmaceutically acceptable, and which may be inert or physiologically active. These compositions can be used orally, parenterally, rectally or topically.

As solid compositions for oral administration, tablets, pills, powders (gelatin capsules, wafer capsules) or granules can be used. In these compositions, the active principle according to the invention is mixed with one or more inert diluents such as starch, cellulose, sucrose, lactose or silica. These compositions can also contain substances other than diluents, e.g. one or more lubricants such as magnesium stearate or talc, a colouring, a coating (dragées) or a lacquer.

As liquid compositions for oral administration, it is possible to use solutions, suspensions, emulsions, syrups and elixirs which are pharmaceutically acceptable, containing inert diluents such as water, ethanol, glycerol, vegetable oils or liquid paraffin. These compositions can contain substances other than diluents, e.g. wetting agents, sweeteners, thickeners, flavourings or stabilizers.

The sterile compositions for parenteral administration can preferably be suspensions, emulsions or non-aqueous solutions. As a solvent or vehicle, it is possible to use water, propylene glycol, a polyethylene glycol, vegetable oils, especially injectable olive oil, injectable organic esters, e.g. ethyl oleate, or other suitable organic solvents. These compositions can also contain adjuvants, especially wetting agents, tonicity regulators, emulsifiers, dispersants and stabilizers. The sterilization can be carried out in several ways, e.g. by aseptic filtration, by incorporating sterilizing agents in the composition, by irradiation or by heating. They can also be prepared in the form of sterile solid compositions which can be dissolved at the time of use in an injectable sterile medium.

The compositions for rectal administration are suppositories or rectal capsules which contain, in addition to the active product, excipients such as cocoa butter, semi-synthetic glycerides or polyethylene glycols.

The compositions for topical administration can be, e.g. creams, ointments, lotions, eyewashes, mouthwashes, nasal drops or aerosols.

In human therapy, the compounds according to the invention are especially useful as anxiolytics.

The doses depend on the effects sought, the period of treatment and the administration route used; they are generally between 20 and 1000 mg per day orally for an adult, with unit doses ranging from 5 to 200 mg of active substance.

In general, the doctor will determine the appropriate dosage in terms of the age and weight and all the other factors specific to the subject to be treated.

The following examples illustrate compositions according to the invention:

EXAMPLE A

The customary technique is used to prepare gelatin capsules containing 50 mg doses of active product and having the following composition:

| | |
|---|---|
| 4-[(2-Phenyl-4-quinolyl)oxyacetyl]morpholine | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

The customary technique is used to prepare tablets containing a 50 mg dose of active product and having the following composition:

| | |
|---|---|
| N—Benzyl-N—methyl-(2-phenyl-4-quinolyl)oxyacetamide | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerin and titanium oxide (72:3.5:24.5) | qs 1 finished film-coated 245-mg tablet. |

EXAMPLE C

An injectable solution is prepared containing 10 mg of active product and having the following composition:

| | |
|---|---|
| 4-[(2-phenyl-4-quinolyl)oxyacetyl]morpholine | 10 mg |
| Benzoic acid | 80 mg |
| Benzyl alcohol | 0.06 cc |
| Sodium benzoate | 80 mg |
| 95% strength ethanol | 0.4 cc |
| Sodium hydroxide | 24 mg |
| Propylene glycol | 1.6 cc |
| Water  qs | 4 cc |

We claim:

1. A racemic or steroisomeric compound of formula

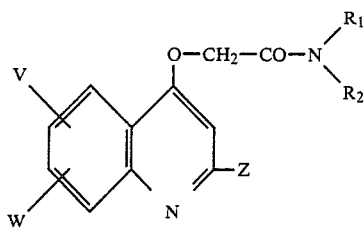

in which
V and W, which may be identical or different, denote hydrogen, halogen, alkyl of 1 to 4 carbon atoms, alkoxy of 1 to 4 carbon atoms, amino, or acylamino of 1 to 4 carbon atoms, Z denotes phenyl, thienyl, pyridyl, or phenyl substituted by one or two substituents selected from halogen, alkyl of 1 to 4 carbon atoms, alkoxy of 1 to 4 carbon atoms, trifluoromethyl, nitro, and amino, but not including more than one nitro, $R_1$ denotes a linear or branched alkyl of 1 to 6 carbon atoms, alkoxyalkyl in which the alkyl and alkoxy portions each have 1 to 4 carbon atoms, cycloalkyl of 3 to 6 carbon atoms, phenyl, phenylalkyl in which the alkyl portion has 1 to 4 carbon atoms, or cycloalkylalkyl in which the alkyl has 1 to 3 carbon atoms and the cycloalkyl portion has 3 to 6 carbon atoms, $R_2$ denotes a linear or branched alkyl of 1 to 6 carbon atoms, alkoxyalkyl in which the alkoxy and alkyl have 1 to 4 carbon atoms each, cycloalkyl of 3 to 6 carbon atoms, phenyl, phenylalkyl in which the alkyl portion has 1 to 4 carbon atoms, or cycloalkylalkyl in which the alkyl has 1 to 3 carbon atoms and the cycloalkyl has 3 to 6 carbon atoms, or a 4-morpholine ring, and $R_1$ and $R_2$ can also form, together with the nitrogen atom to which they are attached: pyrrolidino; piperidino unsubstituted or substituted by hydroxy, alkyl of 1 to 4 carbon atoms, alkoxy of 1 to 4 carbon atoms, or alkyloxycarbonyl in which the alkyl portion has 1 to 4 carbon atoms; morpholino unsubstituted or substituted by one or two alkyls of 1 to 4 carbon atoms; thiomorpholino; piperazino unsubstituted or substituted on the nitrogen atom by alkyl of 1 to 4 carbon atoms, alkyloxycarbonyl in which the alkyl portion has 1 to 4 carbon atoms, acyl of 2 to 5 carbon atoms, or formyl; or a piperazinone ring unsubstituted or substituted on the nitrogen atom by alkyl of 1 to 4 carbon atoms, and also, where it can exist, a salt of such a compound with a pharmaceutically acceptable acid.

2. A compound according to claim 1 which is N-cyclopropylmethyl-N-methyl-(2-phenyl-4-quinolyl)oxyacetamide and its pharmaceutically acceptable acid addition salts.

3. A compound according to claim 1 which is 4-[(2-phenyl-4-quinolyl)oxyacetyl]-2-piperazinone and its pharmaceutically acceptable acid addition salts.

4. A compound according to claim 1 which is 4-[(5-chloro-2-phenyl-4-quinolyl)oxyacetyl]morpholine and its pharmaceutically acceptable acid addition salts.

5. A compound according to claim 1 which is 4-[(2-phenyl-4-quinolyl)oxyacetyl]morpholine and its pharmaceutically acceptable acid addition salts.

6. A compound according to claim 1 which is 4-[(6-acetylamino-2-phenyl-4-quinolyl)oxyacetyl]-morpholine and its pharmaceutically acceptable acid addition salts.

7. A compound according to claim 1 which is N-cyclobutyl-N-methyl-(2-phenyl-4-quinolyl)oxyacetamide and its pharmaceutically acceptable acid addition salts.

8. A pharmaceutical composition useful as an anxiolytic containing, in association with one or more diluents or adjuvants which are compatible and pharmaceutically acceptable, at least one racemic or stereoisomeric compound of formula:

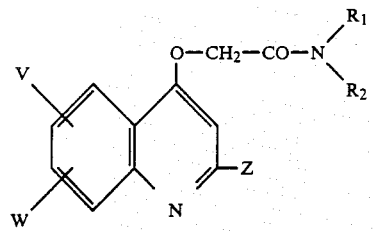

in which
V and W, which may be identical or different, denote hydrogen, halogen, alkyl of 1 to 4 carbon atoms, alkoxy of 1 to 4 carbon atoms, amino, or acylamino of 1 to 4 carbon atoms,
Z denotes phenyl, thienyl, pyridyl, or phenyl substituted by one or two substituents selected from halogen, alkyl of 1 to 4 carbon atoms, alkoxy of 1 to 4 carbon atoms, trifluoromethyl, nitro, and amino, but not including more than one nitro,
$R_1$ denotes a linear or branched alkyl of 1 to 6 carbon atoms, alkoxyalkyl in which the alkyl and alkoxy portions each have 1 to 4 carbon atoms, cycloalkyl of 3 to 6 carbon atoms, phenyl, phenylalkyl in which the alkyl portion has 1 to 4 carbon atoms, or cycloalkylalkyl in which the alkyl portion has 1 to 3 carbon atoms and the cycloalkyl portion has 3 to 6 carbon atoms, $R_2$ denotes a linear or branched alkyl of 1 to 6 carbon atoms, alkoxyalkyl in which the alkoxy and alkyl have 1 to 4 carbon atoms each, cycloalkyl of 3 to 6 carbon atoms, phenyl, phenylalkyl in which the alkyl portion has 1 to 4 carbon atoms, or cycloalkylalkyl in which the alkyl has 1 to 3 carbon atoms and the cycloalkyl has 3 to 6 carbon atoms, or a 4-morpholine ring, and $R_1$ and $R_2$ can also form, together with the nitrogen atom to which they are attached: pyrrolidino; piperidino unsubstituted or substituted by hydroxy, alkyl of 1 to 4 carbon atoms, alkoxy of 1 to 4 carbon atoms, or alkyloxycarbonyl in which the alkyl portion has 1 to 4 carbon atoms; morpholino unsubstituted or substituted by one or two alkyls of 1 to 4 carbon atoms; thiomorpholino; piperazino unsubstituted or substituted on the nitrogen atom by alkyl of 1 to 4 carbon atoms, alkyloxycarbonyl in which the alkyl portion has 1 to 4 carbon atoms, acyl of 2 to 5 carbon atoms, or formyl; or a piperazinone ring unsubstituted or substituted on the nitrogen atom by alkyl of 1 to 4 carbon atoms, or, where it exists, a salt of such a compound with a pharmaceutically acceptable acid.

9. Method of treating anxiety amenable to therapy with a compound capable of binding cerebral type benzodiazepine receptors which comprises administering to a subject in need of anxiolytic therapy an effective amount of a compound as claimed in claim 1.

* * * * *